United States Patent [19]
Stinson

[11] Patent Number: 5,891,191
[45] Date of Patent: Apr. 6, 1999

[54] COBALT-CHROMIUM-MOLYBDENUM ALLOY STENT AND STENT-GRAFT

[75] Inventor: Jonathan S. Stinson, Plymouth, Minn.

[73] Assignee: Schneider (USA) Inc

[21] Appl. No.: 640,253

[22] Filed: Apr. 30, 1996

[51] Int. Cl.$^6$ .................................................. A61F 2/06
[52] U.S. Cl. ................... 623/1; 623/16; 606/194
[58] Field of Search ...................... 623/16, 1; 433/201.1; 606/194

[56] References Cited

U.S. PATENT DOCUMENTS

| | | |
|---|---|---|
| 4,281,419 | 8/1981 | Treace . |
| 4,655,771 | 4/1987 | Wallsten ........................ 623/1 |
| 4,681,110 | 7/1987 | Wiktor ........................ 128/343 |
| 4,731,084 | 3/1988 | Dunn et al. ........................ 623/13 |
| 4,733,665 | 3/1988 | Palmaz ........................ 128/343 |
| 4,800,882 | 1/1989 | Gianturco ........................ 128/343 |
| 4,954,126 | 9/1990 | Wallsten ........................ 606/36 |
| 5,024,232 | 6/1991 | Smid et al. ........................ 128/654 |
| 5,047,050 | 9/1991 | Arpesani ........................ 623/1 |
| 5,061,275 | 10/1991 | Wallsten et al. ........................ 623/1 |
| 5,064,435 | 11/1991 | Porter ........................ 623/12 |
| 5,308,412 | 5/1994 | Shetty et al. ........................ 623/16 |
| 5,382,259 | 1/1995 | Phelps et al. ........................ 606/151 |
| 5,389,106 | 2/1995 | Tower ........................ 606/198 |
| 5,628,787 | 5/1997 | Mayer ........................ 623/1 |
| 5,636,641 | 6/1997 | Fariabi ........................ 128/772 |

FOREIGN PATENT DOCUMENTS

| | | |
|---|---|---|
| WO 91/10766 | 7/1991 | WIPO . |
| WO 92/16166 | 10/1992 | WIPO . |
| WO 94/06372 | 3/1994 | WIPO . |
| WO 94/06373 | 3/1994 | WIPO . |
| WO 94/16646 | 8/1994 | WIPO . |
| WO 94/24961 | 11/1994 | WIPO . |

OTHER PUBLICATIONS

ASTM Standards F75–87 (pp. 25–26), F799–87 (pp. 274–275).
Carpenter Technology Corporation Alloy Data Sheet for Micro–Melt CCM®Plus Alloy (pp. 1–3), (Apr. 21, 1994).
Carpenter Technology Corporation Alloy Data Sheet for BioDur™ Carpenter CCM® Alloy (4 pp), (Feb. 1995).
Carpenter Technology Corporation Alloy Data Sheet for Carpenter CCM® Alloy (10 pp).
Article from Advanced Materials & Process "Cobalt–chromium alloy cuts friction in medical implant" (Jul. 1994) (1 pp).
Kato et al., Experimental Assessement of Newly Devised Transcatheter Stent–Graft for Aortic Dissection, (Ann Thorac Surg 1995;59:98–15).
Albany International Research Co., "Concurrent Engineering of Composites," brochure (13 pp).

Primary Examiner—Paul B. Prebilic
Attorney, Agent, or Firm—Faegre & Benson LLP

[57] ABSTRACT

A self-expanding stent formed of helically wound and braided filaments of wrought cobalt, chromium and molybdenum alloy containing less than about five weight percent nickel. The composition of the alloy from which one embodiment of the stent is formed is Co-26Cr-6Mo-1Si-1Fe-1Mn-1Ni.

47 Claims, 4 Drawing Sheets

COBALT-CHROMIUM-MOLYBDENUM ALLOY STENT AND STENT-GRAFT

BACKGROUND OF THE INVENTION

1. Field of the Invention

The present invention relates generally to implantable, radially expandable medical prostheses including stents and stent-grafts. In particular, the present invention is a cobalt-chromium-molybdenum alloy stent and stent-graft.

2. Description of the Related Art

Medical prostheses frequently referred to as stents and stent-grafts are well known and commercially available. One type of stent, known as a self-expandable stent, is disclosed generally in the Wallsten U.S. Pat. No. 4,655,771, the Wallsten et al. U.S. Pat. No. 5,061,275, International Application Publication Number WO 94/24961, and International Application Publication Number WO 94/16646, all of which are hereby incorporated by reference in their entirety. These devices are used within body vessels of humans and other animals for a variety of medical applications including treating stenosis, maintaining openings in the urinary, biliary, esophageal and renal tracts, and vena cava filters to counter emboli.

Briefly, self-expanding stents of the type described in the above-identified patent documents are formed from a number of resilient filaments or elements which are helically wound and interwoven in a braidlike configuration. The stents assume a substantially tubular form in their unloaded or expanded state when they are not subjected to external forces. When subjected to inwardly-directed radial forces the stents are forced into a reduced-radius and extended-length loaded or compressed state. A delivery device which retains the stent in its compressed state is used to deliver the stent to a treatment site through vessels in the body. The flexible nature and reduced radius of the compressed stent enables it to be delivered through relatively small and curved vessels. After the stent is positioned at the treatment site the delivery device is actuated to release the stent, thereby allowing the stent to self-expand within the body vessel. The delivery device is then detached from the stent and removed from the patient. The stent remains in the vessel at the treatment site.

Materials commonly used for self-expanding stent filaments include Elgiloy® and Phynox® spring alloys. Elgiloy® alloy is available from Carpenter Technology Corporation of Reading Pa. Phynox® alloy is available from Metal Imphy of Imphy, France. Both of these metals are cobalt-based alloys which also include chromium, iron, nickel and molybdenum. Other materials used for self-expanding stent filaments are 316 stainless steel and MP35N alloy which are available from Carpenter Technology corporation and Latrobe Steel Company of Latrobe, Pa., and superelastic Nitinol nickel-titanium alloy which is available from Shape Memory Applications of Santa Clara, Calif.

The yield strength and modulus of elasticity of the filaments forming the self-expanding stent are important characteristics. The spring characteristics of an alloy and stents formed therefrom are determined to a large extent by the modulus of elasticity of the alloy. In general, the modulus of elasticity must be high enough to allow the stent to spring back toward its unloaded state from the compressed state with sufficient radial force to meet the needs of the application for which the stent is designed. The material must also have sufficient strength that it can be compressed for delivery without being plastically deformed or permanently bent. Elgiloy®, Phynox®, MP35N and stainless steel are all high strength and high modulus metals. Nitinol has a relatively lower strength and modulus.

Elgiloy®, Phynox®, MP35N, Nitinol and stainless steel alloys all contain about 10%–20% nickel. Nickel enhances the ductility of the alloys, improving its ability to be mechanically drawn or formed (i.e., reduced in cross-sectional area) into wire of the relatively fine diameters required for stents (between about 0.025 mm and 0.500 mm) by a process known as cold working. Cold working is also desirable because it increases the strength of the material. However, the yield strength that can be obtained by cold working Elgiloy®, Phynox®, MP35N, Nitinol and stainless steel alloys (e.g., about 1738 MPa (252) ksi for Elgiloy® alloy) is generally not high enough for many stent applications. As a result, stents fabricated from the Elgiloy® and Phynox® cold worked (also known as wrought) alloys are typically heat-treated after they are cold worked, a process that significantly increases their yield strength and thereby allows for the fabrication of stents with relatively smaller diameter filaments. By way of example, the yield strength of Elgiloy® alloy can be increased by heat treating to about 2861 MPa (415) ksi. The strength of stainless steel alloys and Nitinol cannot be significantly increased by heat treatment, so these materials are typically not used in the construction of self-expanding stents with high radial strength.

Cold working is a method by which metal is plastically deformed into a particular shape and work (strain) hardened to increase the strength of the material. Processes that can be performed to accomplish cold working are drawing, rolling, extruding, forging, swaging, and the like. Raw material is input into the cold working process in the form of ingots, rods, bars, billets, blanks, or other appropriate shapes. The workpieces are forced to pass through a die, fill a die cavity, or conform to the shape of a die. The output of the cold working process is typically material with a new form and with higher strength and hardness from the metallurgical strain hardening that occurred with the plastic deformation. In a cold working process described in International Publication Number WO 94/16646, billet, bar, rod, or wire is drawn or extruded through a series of round dies and incremental reduction in the material diameter is achieved until the final desired wire size is obtained for stent braiding.

The filaments of the stents described above may form a lattice structure which includes large amounts of open area. In some cases, however, this large open area allows tissue to grow through the stent and occlude portions of the tract that were opened by the stent. For applications where tissue ingrowth of this type is undesirable, as well as for applications in which portions of the tract being treated are weak or have gaps (e.g., aneurysms), it is generally known to use covered stents. Stents or stent-grafts may be covered, for example, by porous membranes, interwoven organic filaments, or the like. Stents of this type are sometimes known as covered stents or stent-grafts, and are disclosed, for example, in *Experimental Assessment of Newly Devised Trans-Catheter Stent-Graf for Aoritic Dissection*, Annual of Thoracic Surgery, M. Kato et al., 59: 908–915 (1995). The membranes incorporated into the stent-grafts are typically formed of polymeric materials. However, many of these polymeric materials can degrade when exposed to temperatures used to heat-treat alloys of the type described above. The need to heat-treat the metal alloy lattice structure and the temperature sensitivities of the polymers used to form the membranes therefore constrain stent-graft designs and their application.

In addition to drawn elongated filaments for interwoven element stents of the type described above and in the Wallsten U.S. Pat. No. 4,655,771, metal alloy materials are drawn or extruded into other forms for stent fabrication. The Palmaz U.S. Pat. No. 4,733,665 relates to a stent fabricated from a drawn or extruded stainless steel tube. The Gianturco U.S. Pat. No. 4,800,882 relates to a stent assembled from a drawn stainless steel wire. Other known stents are fabricated from drawn, extruded, or rolled nickel-titanium alloy ribbon.

Cobalt-chromium-molybdenum (Co-Cr-Mo) alloys have been used in medical implant applications. Chemical, mechanical, and metallurgical requirements for alloys of these types used for surgical implant applications are published in ASTM Standard Designations F 75 and F 799. One such alloy known as BioDur Carpenter CCM® is commercially available from Carpenter Technology Corporation. These chromium-cobalt-molybdenum alloys are highly biocompatible. However, since they have a relatively low nickel content (about 1% maximum), cobalt-chromium-molybdenum alloys have relatively low ductilities and high work hardening rates that limit their formability. For this reason the conventional wisdom has been that these alloys cannot be cold drawn down to the fine wire diameters needed for stents and stent-grafts.

There remains a continuing need for improved stents and stent-grafts. In particular, there is a need for stents and stent-grafts fabricated from highly biocompatible alloys having high yield strengths and high moduli of elasticity. There is also a need for stents and stent-grafts that do not require heat treatment.

SUMMARY OF THE INVENTION

The present invention relates to an improved implantable medical device comprised of a tubular and radially expandable structure including at least one elongate element formed of cobalt-chromium-molybdenum (Co-Cr-Mo) alloy containing less than about five weight percent nickel. The Co-Cr-Mo alloy is highly biocompatible and has a relatively high yield strength and modulus of elasticity.

One embodiment of the invention is a radially self-expandable stent including a plurality of elongate Co-Cr-Mo alloy filaments which are interwoven in a braid-like configuration. The alloy contains at least about 50 weight percent cobalt, between about 26–31 weight percent chromium, between about 4–8 weight percent molybdenum and less than about 2 weight percent nickel.

DETAILED DESCRIPTION OF THE PREFERRED EMBODIMENTS

Figure 1:
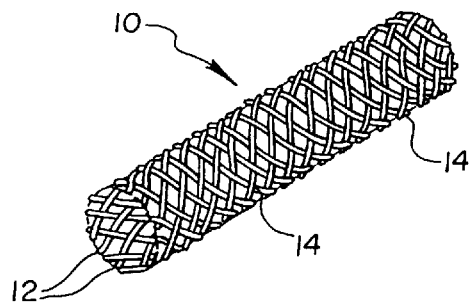
FIG. 1 is an isometric view of an embodiment of the present invention, illustrating a stent having a braided configuration of filaments.
Figure 2:
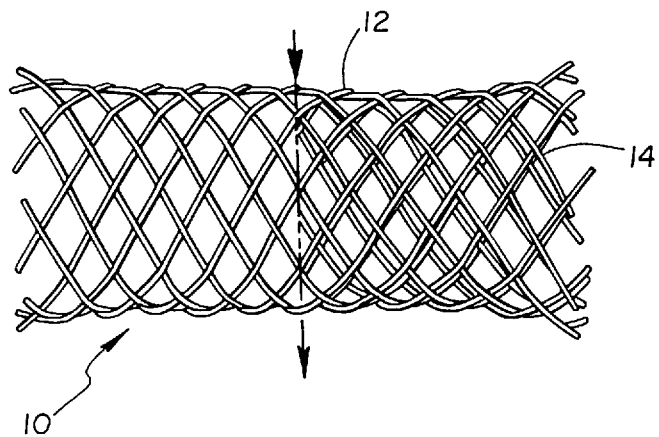
FIG. 2 is a partial longitudinal cross sectional view of the stent shown in FIG. 1.

An implantable prosthesis or stent 10 in accordance with the present invention is illustrated generally in FIGS. 1 and 2. Stent 10 is a tubular device formed from two sets of oppositely-directed, parallel, spaced-apart and helically wound elongated elements or filaments 12. The sets of filaments 12 are interwoven in an over and under braided configuration, and intersect at points such as 14 to form an open lattice structure. The invention is based on the discovery that contrary to conventional wisdom, certain cobalt-chromium-molybdenum (Co-Cr-Mo) alloys containing less than about five weight percent nickel can be drawn or otherwise formed by cold working into wrought elements such as filaments 12 suitable for stents 10. Non-limiting examples of cold working processes which can be used to form such Co-Cr-Mo alloy elements include wire drawing, tube drawing and the like. At least one, and in a preferred embodiment all filaments 12, are formed from commercially available Co-Cr-Mo alloy containing less than two weight percent nickel. Methods for fabricating stents 10 are generally known and disclosed, for example, in the Wallsten U.S. Pat. No. 4,655,771, the Wallsten et al. U.S. Pat. No. 5,061,275, and International Application Publication Numbers WO 94/24961 and WO 94/16646, which are hereby incorporated by reference in their entirety.

Stent 10 is shown in its expanded or relaxed state in FIGS. 1 and 2, i.e., in the configuration it assumes when subjected to no external loads or stresses. The filaments 12 are resilient, permitting the radial compression of stent 10 into a reduced-radius, extended-length configuration or state suitable for delivery to the desired placement or treatment site through a body vessel (i.e., transluminally). Stent 10 is also self-expandable from the compressed state, and axially flexible.

Stated another way, stent 10 is a radially and axially flexible tubular body having a predetermined diameter that is variable under axial movement of the ends of the body relative to each other. The stent 10 is composed of a plurality of individually rigid but flexible and elastic thread elements or filaments 12, each of which extends in a helix configuration along a longitudinal center line of the body as a common axis. At least one, and in a preferred embodiment all of filaments 12 are formed from Co-Cr-Mo alloy containing less than about five weight percent nickel. The filaments 12 define a radially self-expanding body. The body is provided by a first number of filaments 12 having a common direction of winding but axially displaced relative to each other, and crossing a second number of filaments 12 also axially displaced relative to each other but having an opposite direction of winding.

The tubular and self-expandable body or structure formed by the interwoven filaments 12 is a primary prosthetically-functional structure of stent 10, and for this reason the device can be considered to substantially consist of this structure to the exclusion of other structures. However, it is known that other structures and features can be included in stents, and in particular features which enhance or cooperate with the tubular and self-expandable structure or which facilitate the implantation of the structure. One example is the inclusion of radiopaque markers on the structure which are used to visualize the position of the stent through fluoroscopy during implantation. Other examples include collapsing threads or other structures to facilitate repositioning and removal of the stent. Stents of these types nonetheless still substantially consist of the tubular and self-expandable structure formed by interwoven filaments 12 and shown in FIGS. 1 and 2. Furthermore, many of the desirable properties and features of stent 10 will be present if some, but not all, of the filaments 12 consist of the Co-Cr-Mo alloy.

Figure 3:
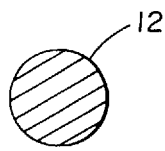
FIG. 3 is a cross-sectional view of one of the filaments of the stent shown in FIG. 1.

FIG. 3 is a cross-sectional view of one embodiment of the Co-Cr-Mo alloy filaments 12. As shown, the filaments 12 are substantially homogeneous in cross section. Commercially available alloys may have minor fluctuations in component concentration while remaining substantially homogeneous. The composition of filaments 12 can also be homogeneous in the lengthwise direction.

Figure 4:
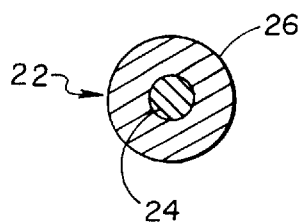
FIG. 4 is a cross-sectional view of a composite filament in accordance with another embodiment of the invention.

FIG. 4 is a cross-sectional illustration of a composite filament 22 which includes a central core 24 and a case 26 surrounding the core. Filaments 22 can be used to fabricate stents such as 12, and are described in greater detail in International Application Number WO 94/16646. Core 24 or case 26 can be formed from the wrought Co-Cr-Mo alloy described herein. One preferred embodiment of a stent such as 12 is formed from composite filaments 24 having cases 26 of the wrought Co-Cr-Mo alloy.

The filaments 12 can be formed from a wide variety of Co-Cr-Mo alloys containing less than about five weight percent nickel, preferably containing less than about two weight percent nickel, and more preferably containing no more than about one weight percent nickel. The alloys can include nitrogen (N) in an amount between about 0.00 weight percent and about 0.25 weight percent, and carbon (C) in an amount between about 0.00 weight percent and about 0.35 weight percent. In one embodiment, between about 0.15–0.20 weight percent nitrogen and between about 0.01–0.10 weight percent carbon can be used. The amount of Cr in the alloy can range up to a maximum of about 31.0 weight percent, and is preferably contained in an amount between about 26.0 weight percent and 30.0 weight percent. The amount of Mo in the alloy can range up to a maximum of about 8.0 weight percent, and is preferably contained in an amount between about 5.0 weight percent and about 7.0 weight percent. Other elements that can be contained in the Co-Cr-Mo alloy, preferably is quantities no greater than about 1.0 weight percent, are iron (Fe), silicon (Si), manganese (Mn), copper (Cu), phosphorous (P), sulfur (S) and tungsten (W). The balance of the alloy composition can be Co, which is preferably contained in an amount of at least 60.0 weight percent.

Any known or otherwise conventional cold working process can be used to form the filaments 12 and 22. Non-limiting examples include drawing, rolling, extruding, forging, swaging, and the like. The Co-Cr-Mo alloy can be input into the cold working process in the form of ingots, rods, bars, billets, blanks or other appropriate shapes.

Sample filaments 12 were cold drawn from BioDur Carpenter CCM® alloy which is commercially available from Carpenter Technology Corporation of Reading, Pa. The published composition of this alloy is Co, 26 Cr, 6 Mo, 1 Si, 1 Fe, 1 Mn, 1 Ni, 0.5 W, 0.5 Cu, 0.18 N, 0.05 C, 0.015 P, 0.015 S. The filaments 12 were taken from wire of this alloy having a nominal diameter of about 0.0039 inch (0.1 mm) that was final cold drawn to about 50%–80% reduction in area by Fort Wayne Metals Research Products Corporation of Fort Wayne, Ind. The ultimate tensile strength of this as drawn wire was measured and found to be about 2889 MPa (419 ksi). The measured yield strength of samples of the as drawn wire was 2489 MPa (361 ksi). The measured elongation of the as drawn wire samples was 2.4%. The measured modulus of elasticity of the samples was 168,238 MPa (24.4 msi). The measured mean bend modulus of the as drawn sample was 157,896 MPa (22.9 msi). The measured mean shear modulus of the as drawn samples was 85,884 MPa (12.5 msi).

A number of the CCM® alloy samples were also heat-treated in argon. A wire sample heat-treated for about thirty minutes at 500° C. was tested and found to have an ultimate tensile strength of about 3185 MPa (462 ksi), a yield strength of about 3068 MPa (445 ksi) an elongation of about 2%, and a modulus of elasticity of about 193,750 MPa (28.1 msi). A sample heat-treated for about thirty minutes at 600° C. was tested and found to have an ultimate tensile strength of about 3172 MPa (460 ksi), a yield strength of about 2992 MPa (434 ksi) an elongation of about 2%, a modulus of elasticity of about 204,092 MPa (29.6 msi), a mean bend modulus of about 170,609 MPa (24.7 msi) and a mean shear modulus of about 96,627 MPa (14.0 msi). Yet another wire sample heat-treated for about thirty minutes at 700° C. was tested and found to have an ultimate tensile strength of about 2965 MPa (430 ksi), a yield strength of about 2710 MPa (393 ksi) an elongation of about 2%, and a modulus of elasticity of about 207,540 MPa (30.1 msi).

The yield strength and modulus of elasticity of the sample as drawn CCM® alloy wire are generally similar to those of heat-treated Elgiloy® alloy wire of a similar diameter. Stents fabricated with the CCM® alloy wire can therefore have spring characteristics, radial pressure and wire strength and stresses (i.e., properties) similar to those of similarly sized stents fabricated from Elgiloy® alloy wire. Equivalent physical stent characteristics can thereby be obtained from a stent that has a relatively low nickel content. Furthermore, relatively high strength levels were achieved solely by cold working the alloy. Stents fabricated from the CCM® alloy wire need not therefore be heat treated to achieve the strength levels required for certain applications.

Another desirable characteristic of the CCM® alloy wire is that it has a high surface hardness and smooth surface finish. In the as drawn state, the measured hardness values of samples of the CCM® alloy wire were between about 46.2 and about 48.7 Rockwell C Scale, and averaged about 47.3 Rockwell C Scale. Heat treated samples of the CCM® alloy wire had measured hardness values between about 55.2 and 57.8 Rockwell C Scale, and averaged about 56.6 Rockwell C Scale. These hardness values are relatively high compared to stainless steel (about 34–40 Rockwell C Scale when as drawn) and Elgiloy® alloy (about 42.2–44 Rockwell C Scale when as drawn, and about 53.7–55.4 Rockwell C Scale when aged). These relatively high surface hardness characteristics are advantageous in self-expanding stents since they improve the wear resistance of the filaments 12 and reduce the friction at the points 14 at which the filament intersect one another in stent 10.

Figure 5:
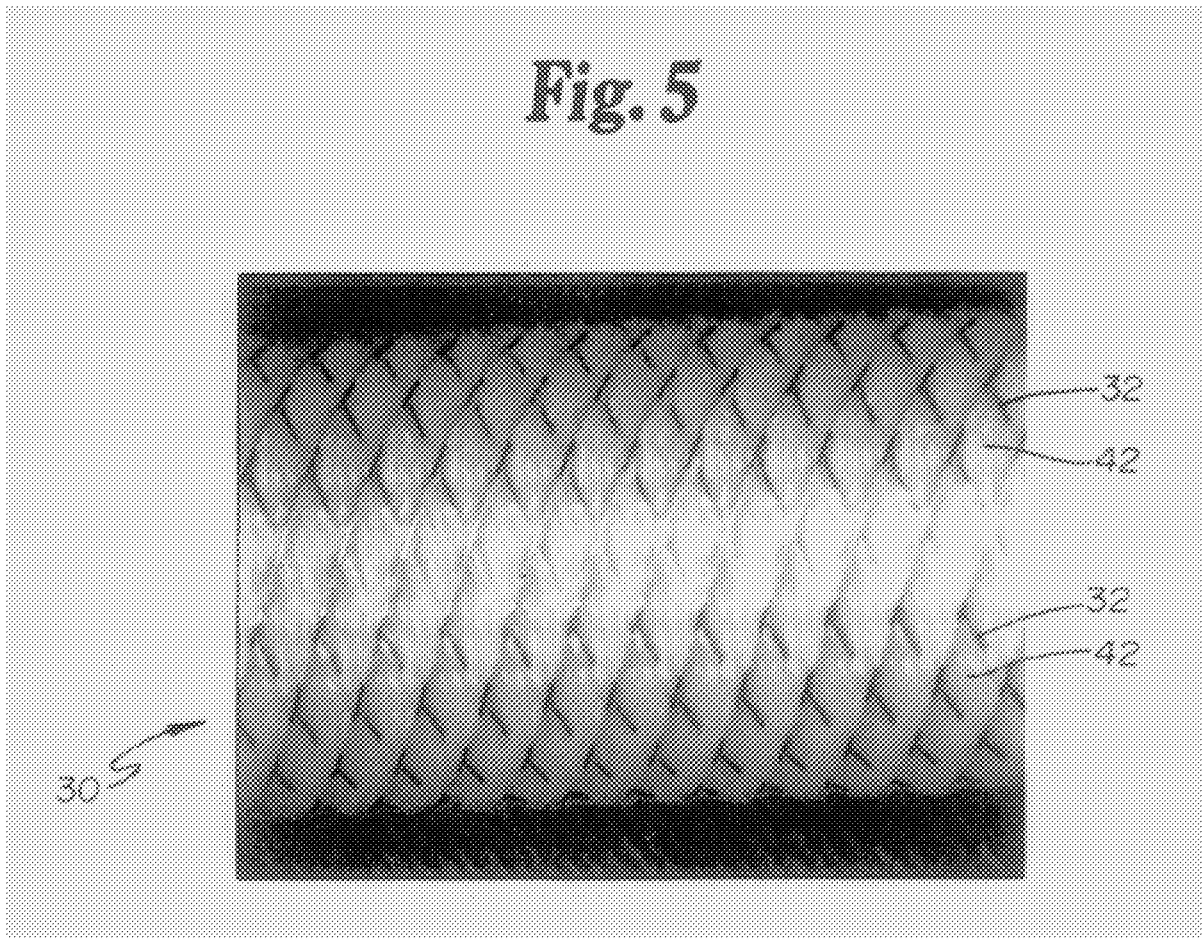
FIG. 5 is a photograph of a stent-graft in accordance with the present invention.

FIG. 5 is an illustration of a stent-graft or prosthesis 30 which includes Co-Cr-Mo alloy structural filaments or strands 32 of the type incorporated into stent 10 and described above (e.g., filaments 12). As shown, the structural Co-Cr-Mo alloy strands 32 are interbraided with layers of more tightly woven textile strands 42 that reduce permeability. The structural strands 32 are selectively shaped before their interbraiding with the textile strands 42, either by a thermal set or by selective plastic deformation, and in either event are shaped without adversely affecting the textile strands. Plastic deformation of structural strands 32 by cold working is advantageous in permitting a continuous process of cold working followed by interbraiding. The result is an interbraided prosthesis incorporating the strength, resilience and range of radii associated with self-expanding stents without the need for an age-hardening heat treatment, and the impermeability associated with vascular grafts. Prostheses such as 30 and associated methods of manufacture are described in detail in the commonly assigned P. Thompson U.S. patent applications Ser. No. 08/640,091 entitled "Three-Dimensional Braided Covered Stent" and Ser. No. 08/640,062 entitled "Braided Composite Prosthesis", both of which are filed on even date herewith and expressly incorporated herein by reference in their entirety.

Figure 6:
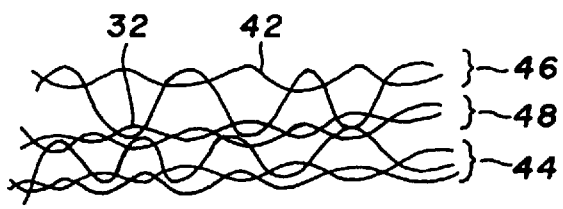
FIG. 6 is a schematic illustration of several discrete layers which can be formed by the three-dimensional braiding of multiple strands and incorporated into the stent-graft shown in FIG. 5.

FIG. 6 schematically illustrates the manner in which multiple structural strands 32 and multiple textile strands 42 are interbraided with one another to form several discrete layers of prosthesis 30. These include an inner (radially inward) layer 44 consisting primarily of textile strands 42, an outer layer 46 also consisting primarily of the textile strands, and a medial layer 48 that incorporates the structural strands 32. Layers 44–48 are formed simultaneously in a single braiding operation that also interlocks the layers, in that at least one of the strands from each of the layers is braided into one of the other layers. In one preferred approach, inner layer 44 and outer layer 46 are formed substantially entirely of textile strands 42, while medial layer 48 is an interbraided combination of textile strands 42 and structural strands 32, e.g. at a one-to-one ratio, or two-to-one ratio in favor of the textile strands. Inner layer 44 includes a first set of its textile strands that extend into the medial layer, and a second set of its textile strands that extend through the medial layer into the outer layer, then back to the inner layer. These sets together can comprise a relatively small percentage of the textile strands of layer 44. Medial layer 48 and outer layer 46 similarly have sets of textile strands extending into the other layers. Thus there is a substantial intermingling among strands of the different layers for effective interlocking, although the layers remain distinct from one another in character.

Textile strands 42 preferably are multifilament yarns, although they can be monofilaments. In either event the textile strands are much finer than the structural strands 32, ranging from about 10 to 400 denier. Individual filaments of the multifilament yarns can range from about 0.25 to about 10 denier. The multifilament yarns generally have a high degree of compliance, which may or may not include elasticity. Suitable materials include PET, polypropylene, polyurethane, polycarbonate urethane, HDPE, polyethene, silicone, PTFE, ePTFE and polyolefin. One suitable high molecular weight polyethylene is sold under the brand name "Spectra". The fine textile strands are closely woven in layers 44, 46, and 48, and can be considered to form a textile sheeting or fabric in each layer.

Due to the fineness of textile strands 42 and a close or tight weave, the textile sheetings can be microporous, yet essentially impervious to body fluids. Also, the textile sheeting layers are highly compliant, conforming to changes in the shape of latticework formed by structural strands 32 as prosthesis 30 either radially self-expands or is radially compressed. The shape of the latticework thus determines the shape of the prosthesis 30.

A particularly favorable structure for prosthesis 30 has a medial layer 48 formed by interbraiding metallic structural strands 32 with Dacron (polyester) multifilament yarns as the textile strands 42. The metal structural strands exhibit high strength in terms of elastic moduli. In contrast, polyethylene, for example, has an elastic modulus in the range of about $0.02$–$0.055 \times 10^6$ psi, and other polymeric materials have elastic moduli in this order of magnitude. Accordingly, for a given strand diameter, helical diameter and helical pitch, a latticework of metallic strands is considerably more resistant to radial compression, and provides a greater residual force for acute fixation. The Dacron polyester multifilament yarn has a high elastic recovery and elongation (up to 36% for the polyester fiber) and a low elastic modulus, which ensure that textile sheeting 40 conforms to the latticework.

Figure 7:
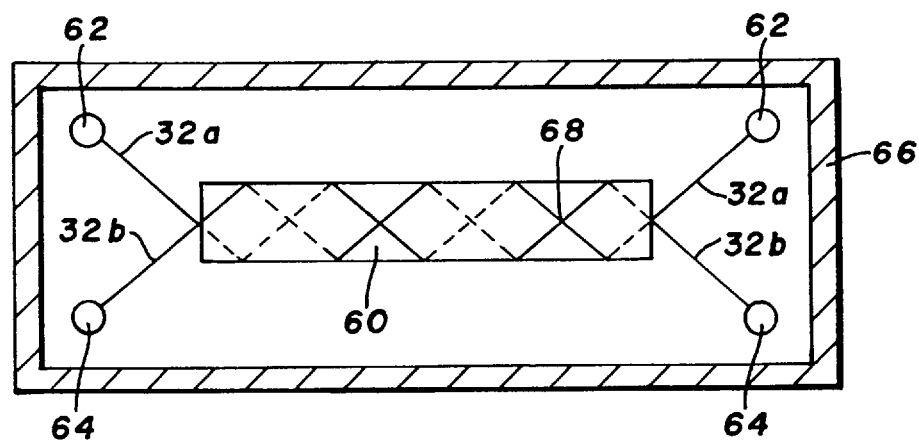
FIGS. 7–9 schematically illustrate a process for manufacturing the stent-graft shown in FIG. 5.
Figure 8:
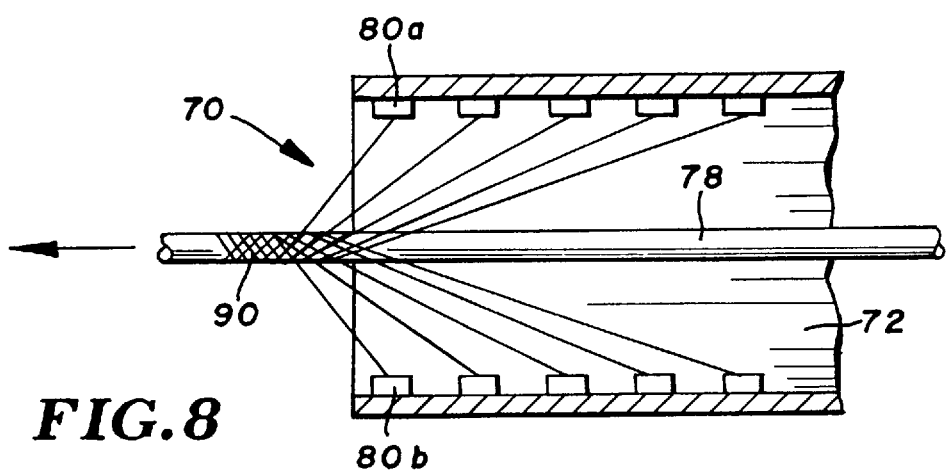
Figure 9:
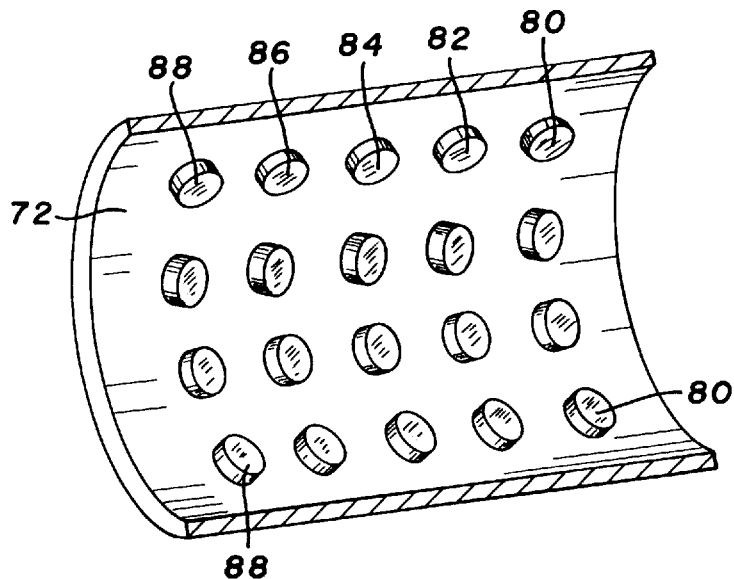

To attain favorable characteristics of stents and grafts, prosthesis 30 can be fabricated according to several steps as illustrated in FIGS. 7–9. FIG. 7 shows two structural strands (metal monofilaments) 32a and 32b, one from each set of oppositely directed structural strands, wound about a mandrel 60 and supported by respective bobbins 62 and 64. While just strands 32a and 32b are illustrated as a matter of convenience, it is to be appreciated that all of the structural strands are wound about the mandrel and maintained together for shaping. Only structural strands are present, however, as shaping occurs before interbraiding with the textile strands.

Age-hardening is accomplished within a furnace 66 in a vacuum or a protective atmosphere. Temperatures are within the range of about 350°–1000° C., with the specific temperature depending on the structural material. The filaments overlie one another to form multiple intersections, one of which is indicated at 68. Bobbins, including 62 and 64, are set to tension their respective strands during age-hardening. The appropriate duration for age-hardening varies with materials and dimensions, but can range from as brief as 30 seconds, to about 5 hours.

After age-hardening, the structural strands are allowed to cool, whereupon each structural strand retains the helical shape as its nominal shape. In the context of elastic materials, "nominal shape" refers to the shape in a relaxed state, i.e. when under no external stress. The age-hardened metallic monofilaments are highly resilient, i.e. deformable under external stress, but elastically returning to the nominal shape when free of the external stress.

Interbraiding of the structural strands 32 and textile strands 42 occurs after selective shaping. FIG. 8 schematically illustrates a braiding apparatus 70 including a cylindrical carrier assembly 72 including several annular arrays of bobbins, two of the bobbins being indicated at 80a and 80b. The apparatus further includes a mandrel 78, centered within the cylindrical assembly and movable longitudinally relative to the assembly as indicated by the arrow.

FIG. 9 illustrates part of carrier assembly 72 in greater detail, to reveal five annular arrays or sets of carrier bobbins indicated at 80, 82, 84, 86 and 88. The sets are coaxial and axially spaced apart, each including forty-eight bobbins, twenty-four bobbins for respective clockwise and counterclockwise windings about mandrel 78. While those skilled in the art are acquainted with the use of braiding machinery, it is emphasized here that braiding apparatus 70 is configured as described in the aforementioned International Patent Publication No. WO91/10766. Suitable braiding machinery is available from Albany International Research Company of Mansfield, Mass.

Figure 10:
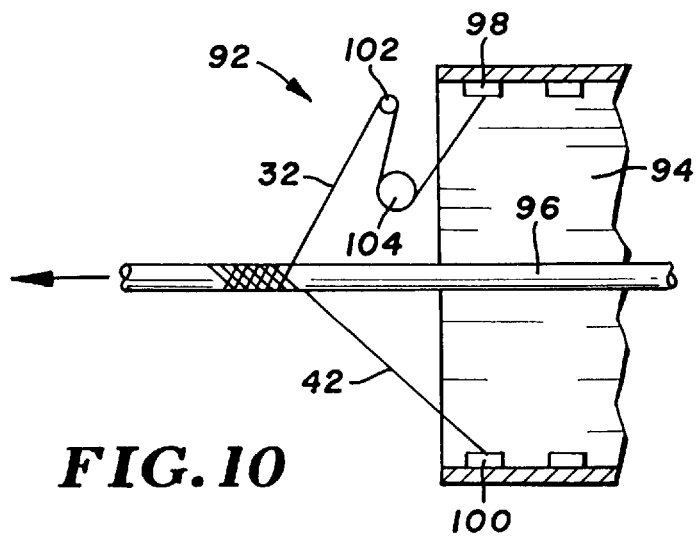
FIG. 10 schematically illustrates an alternative process for manufacturing the stent-graft shown in FIG. 5.

FIG. 10 schematically illustrates an alternative three-dimensional braiding apparatus 92 in which the structural strands are selectively shaped by cold working. In particular, a cylindrical carrier assembly 94 is mounted concentrically on a longitudinally movable mandrel 96. As before, the carrier assembly supports multiple bobbins in arrays including several concentric circular sets of bobbins, with two of the bobbins being indicated at 98 and 100. A structural strand 32 has been wound on the bobbin 98, while bobbin 100 carries a textile strand 42. The structural strand is not thermally shaped before braiding, and thus at first has a linear nominal shape.

Structural strand 32 is plastically deformed by cold working as it travels from bobbin 98 to the mandrel. A small diameter shaping pulley 102 and a larger diameter idler pulley 104 are disposed along the path traversed by strand 32. While pulleys 102 and 104 are shown in side elevation in FIG. 10, it should be understood that in the actual braiding device pulley 102 is orthogonal to pulley 104 to effect the selected shaping of strand 32. Shaping pulley 102 exerts a bending stress on the moving structural strand trained about this pulley, particularly on radially outward portions of the strand. Bobbin 98 is supported on a carrier that includes a clutch (not shown) adjustable to adjust the tension applied to the strand, thereby to adjust the amount of bending stress.

The tension is controlled so that the bending stress, at least along the radially outward portions of the strand along pulley 102, exceeds the yield stress of the material. The appropriate level of tension is in the range of about 200–1000 gms, depending on such factors as the material, the monofilament diameter and the bending radius about pulley 102. The result is a cold-working plastic deformation. The plastic flow is continuous, and changes the nominal shape of the structural strand from linear to helical. Further in this connection, it is noted that pulley 102 would impart a curved nominal shape to the structural strand in any event, and that the helical nominal shape with the desired pitch is obtained through proper orientation of the pulley with respect to the carrier assembly while maintaining the desired tension in the strand. No post-braiding age-hardening heat treatment is necessary when structural metal filaments with sufficiently high yield strength and modulus are utilized, such as the Co-Cr-Mo alloy filament described herein.

Although the present invention has been described with reference to preferred embodiments, those skilled in the art will recognize that changes can be made in form and detail without departing from the spirit and scope of the invention. In particular, balloon-expandable and other stents fabricated in accordance with the present invention with elements formed of Co-Cr-Mo alloy containing less than about five weight percent nickel will also offer important advantages.

What is claimed is:

1. An implantable stent or stent graft medical device comprised of a tubular and radially expandable structure including at least one elongate element having a diameter between about 0.025 mm and about 0.500 mm and formed of cobalt, chromium and molybdenum (Co-Cr-Mo) alloy containing cobalt as a primary element, chromium as a secondary element and molybdenum as a ternary element and containing less than about 5 weight percent nickel.

2. The medical device of claim 1 wherein the Co-Cr-Mo alloy contains less than about 2 weight percent nickel.

3. The medical device of claim 1 wherein the Co-Cr-Mo alloy contains a maximum of about 1 weight percent nickel.

4. The medical device of claim 1 wherein the Co-Cr-Mo alloy contains between about 0 and about 0.25 weight percent nitrogen (N), and between about 0 and about 0.35 weight percent carbon (C).

5. The medical device of claim 4 wherein the Co-Cr-Mo alloy contains between about 0.15 and about 0.20 weight percent nitrogen (N), and between about 0.01 and about 0.10 weight percent carbon.

6. The medical device of claim 1 wherein the structure substantially consists of the at least one Co-Cr-Mo alloy element.

7. The medical device of claim 1 wherein each elongate Co-Cr-Mo element is formed of an at least 50% diameter-reduced filament.

8. The medical device of claim 1 wherein each Co-Cr-Mo element is characterized by an as drawn hardness of at least 45.5 Rockwell C Scale.

9. The medical device of claim 8 wherein each Co-Cr-Mo element is free from post-drawing heat treatment.

10. The medical device of claim 1 wherein each Co-Cr-Mo element is free from post-drawing heat treatment.

11. The medical device of claim 1 wherein the device is further comprised of a lattice structure including the at least one elongate element formed of Co-Cr-Mo alloy.

12. The medical device of claim 1 wherein the radially self-expandable structure is self-expanding.

13. The medical device of claim 1 wherein the Co-Cr-Mo alloy contains at least about 50 weight percent cobalt between about 25–31 weight percent chromium, between about 4–8 weight percent molybdenum, between about 0.15–0.20 weight percent nitrogen and between about 0.01–0.10 weight percent carbon.

14. The medical device of claim 13 wherein the Co-Cr-Mo alloy contains less than about 2 weight percent nickel.

15. The medical device of claim 14 wherein the Co-Cr-Mo alloy contains a maximum of about 1 weight percent nickel.

16. The medical device of claim 13 wherein each elongate element is formed of an at least 50% diameter-reduced filament.

17. The medical device of claim 13 wherein each Co-Cr-Mo alloy element is free from post-drawing heat treatment.

18. The medical device of claim 1 wherein the device further includes a membrane of porous material coextensive with at least a portion of the length of the expandable structure.

19. The medical device of claim 18 wherein the membrane is formed of polymeric material.

20. The medical device of claim 18 wherein each Co-Cr-Mo alloy element is free from post-drawing heat treatment.

21. The medical device of claim 13 wherein the device is further comprised of a lattice structure including the at least one elongate element formed of Co-Cr-Mo alloy.

22. The medical device of claim 13 wherein the radially self-expandable structure is self-expanding.

23. The medical device of claim 1 wherein the Co-Cr-Mo alloy contains at least about 60 weight percent cobalt, about 26 weight percent chromium, about 6 weight percent molybdenum, about 1 weight percent silicon, about 1 weight percent iron, about 1 weight percent manganese, about 1 weight percent nickel, about 0.18 weight percent nitrogen and about 0.05 weight percent carbon.

24. The medical device of claim 23 wherein each elongate element is formed of an at least 50% diameter-reduced filament.

25. The medical device of claim 23 wherein the device is free from post-drawing heat treatment.

26. The medical device of claim 23 wherein the device further includes a membrane of porous material coextensive with at least a portion of the length of the expandable structure.

27. The medical device of claim 26 wherein the membrane is formed of polymeric material.

28. The medical device of claim 27 wherein the device is free from post-drawing heat treatment.

29. The medical device of claim 23 wherein each Co-Cr-Mo element is characterized by an as drawn hardness of at least 45.5 Rockwell C Scale.

30. The medical device of claim 23 wherein the device is further comprised of a lattice structure including the at least one elongate element formed of Co-Cr-Mo alloy.

31. The medical device of claim 23 wherein the radially self-expandable structure is self-expanding.

32. An implantable stent or stent graft medical device comprising a tubular, radially compressible, axially flexible and a radially self-expandable structure including a plurality of elongate filaments having a diameter between about 0.025 mm and about 0.500 mm and formed of cobalt, chromium and molybdenum (Co-Cr-Mo) alloy containing at least about 50 weight percent cobalt as a primary element, between about 26–31 weight percent chromium as a secondary element, between about 4–8 weight percent molybdenum as a ternary element, between about 0.15–0.20 weight percent nitrogen, between about 0.01–0.10 weight percent carbon and less than about 2 weight percent nickel said plurality of elongate filaments are interwoven.

33. The medical device of claim 32 wherein the Co-Cr-Mo alloy filaments are free from post-drawing heat treatment.

34. The medical device of claim 32 wherein each elongate filament is formed of an at least 50% diameter-reduced filament.

35. The medical device of claim 32 wherein the Co-Cr-Mo alloy filaments contain a maximum of about 1 weight percent nickel.

36. The medical device of claim 32 wherein each Co-Cr-Mo filament is characterized by an as drawn hardness of at least 45.5 Rockwell C Scale.

37. The medical device of claim 32 wherein the Co-Cr-Mo alloy contains at least about 60 weight percent cobalt, about 26 weight percent chromium, about 6 weight percent molybdenum, about 1 weight percent silicon, about 1 weight percent iron, about 1 weight percent manganese, about 1 weight percent nickel, about 0.18 weight percent nitrogen and about 0.05 weight percent carbon.

38. The medical device of claim 37 wherein the Co-Cr-Mo alloy filaments are free from post-drawing heat treatment.

39. The medical device of claim 37 wherein each elongate filament is formed of an at least 50% diameter-reduced filament.

40. The medical device of claim 37 and further including a plurality of elongate organic filaments interwoven with one another and the Co-Cr-Mo alloy filaments.

41. The medical device of claim 40 wherein the organic filaments are formed of polymeric material.

42. The medical device of claim 41 wherein the device is free from post-interweaving heat treatment.

43. The medical device of claim 19 wherein the membrane is formed from a plurality of elongate or organic filaments interwoven with one another and the Co-Cr-Mo alloy filaments.

44. The medical device of claim 43 wherein the device is free from post-interweaving heat treatment.

45. The medical device of claim 27 wherein the membrane is formed from a plurality of elongate or organic filaments interwoven with one another and the Co-Cr-Mo alloy filaments.

46. The medical device of claim 45 wherein the device is free from post-interweaving heat treatment.

47. An implantable stent or stent graft medical device comprising a tubular, radially compressible, axially flexible and a radially self-expandable structure including a plurality of elongate filaments having a diameter between about 0.025 mm and about 0.500 mm and formed of cobalt, chromium and molybdenum (Co-Cr-Mo) alloy containing at least about 50 weight percent cobalt as a primary element, between about 26–31 weight percent chromium as a secondary element, between about 4–8 weight percent molybdenum as a ternary element, between about 0.15–0.20 weight percent nitrogen, between about 0.01–0.10 weight percent carbon and less than about 0.5 weight percent nickel said plurality of elongate filaments are interwoven.

\* \* \* \* \*

UNITED STATES PATENT AND TRADEMARK OFFICE
CERTIFICATE OF CORRECTION

PATENT NO. : 5,891,191
DATED : April 6, 1999
INVENTOR(S) : Stinson

It is certified that error appears in the above-identified patent and that said Letters Patent is hereby corrected as shown below:

Column 9, line 49, after "nickel" insert -- said plurality of elongate elements forming a lattice structure --

Column 10, line 14, after "cobalt", insert -- , --

Signed and Sealed this

Twenty-first Day of September, 1999

Attest:

Q. TODD DICKINSON

*Attesting Officer*     *Acting Commissioner of Patents and Trademarks*